(12) United States Patent
Molander et al.

(10) Patent No.: US 7,217,260 B2
(45) Date of Patent: May 15, 2007

(54) ABSORBENT ARTICLE WITH TENSION-DIVIDING SIDE PANELS

(75) Inventors: John C. Molander, Cincinnati, OH (US); Larry K. Johnson, Milford, OH (US)

(73) Assignee: The Procter & Gamble Co., Cincinnati, OH (US)

( * ) Notice: Subject to any disclaimer, the term of this patent is extended or adjusted under 35 U.S.C. 154(b) by 249 days.

(21) Appl. No.: 09/773,241

(22) Filed: Jan. 31, 2001

(65) Prior Publication Data

US 2002/0103470 A1    Aug. 1, 2002

(51) Int. Cl.
  *A61F 13/15* (2006.01)
  *A61F 13/20* (2006.01)
(52) U.S. Cl. .................... 604/385.24; 604/385.29; 604/385.3
(58) Field of Classification Search ........... 604/385.29, 604/385.3, 385.24, 385.11, 385.01
  See application file for complete search history.

(56) References Cited

U.S. PATENT DOCUMENTS

| | | | | |
|---|---|---|---|---|
| 2,743,725 | A | 5/1956 | Matthews | 128/284 |
| 4,010,754 | A | 3/1977 | Pieniak | 128/287 |
| 4,090,516 | A | 5/1978 | Schaar | 128/287 |
| 4,568,344 | A | 2/1986 | Suzuki et al. | 604/389 |
| 4,731,066 | A * | 3/1988 | Korpman | 604/366 |
| 4,826,499 | A | 5/1989 | Ahr | 604/389 |
| 4,850,988 | A | 7/1989 | Aledo et al. | 604/385.1 |
| 4,857,067 | A | 8/1989 | Wood et al. | 604/389 |
| 4,911,702 | A | 3/1990 | O'Leary et al. | 604/389 |
| 4,937,887 | A | 7/1990 | Schreiner | 2/402 |
| 4,940,462 | A | 7/1990 | Salerno | 604/387 |
| 5,245,436 | A | 9/1993 | Alattar | 358/182 |
| 5,370,634 | A | 12/1994 | Ando et al. | 604/385.1 |
| 5,496,298 | A | 3/1996 | Kuepper et al. | 604/389 |
| 5,536,555 | A | 7/1996 | Zelazoski et al. | 428/138 |
| 5,554,145 | A | 9/1996 | Roe et al. | 604/385.2 |
| 5,580,411 | A | 12/1996 | Nease et al. | 156/260 |
| 5,593,401 | A | 1/1997 | Sosalla et al. | 604/385.2 |
| 5,669,897 | A | 9/1997 | Lavon et al. | 604/385.2 |
| 5,804,021 | A | 9/1998 | Abuto et al. | 156/252 |
| 5,827,260 | A | 10/1998 | Suzuki et al. | 604/385.2 |
| 5,899,895 | A * | 5/1999 | Robles et al. | 604/385.29 |
| 5,906,008 | A * | 5/1999 | Heki et al. | 2/400 |
| 6,132,411 | A | 10/2000 | Huber et al. | 604/385.29 |

FOREIGN PATENT DOCUMENTS

EP    0 323 040    7/1989

(Continued)

*Primary Examiner*—Michele Kidwell
(74) *Attorney, Agent, or Firm*—George Leal; Laura L. Whitmer; Matthew P. Fitzpatrick (57) ABSTRACT

Absorbent articles such as disposable diapers, incontinent briefs, diaper holders, training pants, and the like, that provide dynamic fit about the wearer by the use of extensible, outwardly extending side panels. The side panel includes at least one discontinuity for dividing the tensile force extending the side panel into a waist-directing force and a leg-directing force. The waist-directing force is transmitted by the side panel to the waist area of the article to maintain the waist area in a snug, but comfortable, fit against the waist of the wearer. The leg-directing force is transmitted by the side panel to the leg cuff area of the article to prevent leakage between the leg cuff and the wearer's leg.

8 Claims, 5 Drawing Sheets

FOREIGN PATENT DOCUMENTS

| | | |
|---|---|---|
| JP | 2682969 | 11/1997 |
| JP | 10-5276 | 1/1998 |
| JP | 10-57414 | 3/1998 |
| JP | 10-57415 | 3/1998 |
| WO | WO 92/22274 | 12/1992 |
| WO | WO 94/07450 | 4/1994 |
| WO | WO 94/28840 | 12/1994 |
| WO | WO 94/28841 | 12/1994 |
| WO | WO 96/21412 | 7/1996 |
| WO | WO 96/29038 | 9/1996 |
| WO | WO 98/55062 | 12/1998 |
| WO | WO 99/33427 | 7/1999 |

* cited by examiner

ABSORBENT ARTICLE WITH TENSION-DIVIDING SIDE PANELS

FIELD OF THE INVENTION

The present invention relates to absorbent articles that are worn, such as diapers, incontinent briefs, diaper holders, training pants, sanitary napkins, and the like. More particularly the present invention relates to absorbent articles having side panels having at least one discontinuity for reducing or changing the transmission of tensile forces within the side panel in order to distribute the tensile forces to the waist area of the article and to the leg cuff area of the article to provide improved fit of the article and improved comfort for the wearer.

BACKGROUND OF THE INVENTION

Infants and other incontinent individuals wear absorbent articles such as diapers and incontinent briefs to receive and contain discharged urine and other body exudates. Such absorbent articles function both to contain the discharged materials and to isolate those materials from the body of the wearer and from the wearer's articles and bed clothing. Disposable absorbent articles having many different basic designs are known in the art. For example, U.S. Pat. No. Reissue Re. 26,152, entitled "Disposable Diaper," which issued on Jan. 31, 1967, to Duncan et al., describes a basic disposable diaper structure that has achieved wide acceptance and considerable commercial success. Additionally, U.S. Pat. No. 5,151,092, entitled "Absorbent Article With Dynamic Elastic Waist Feature Having a Predisposed Resilient Flexural Hinge," which issued on Sep. 29, 1992, to Buell et al., describes an absorbent article having an elastic waist feature for improving dynamic fit as well as improving containment characteristics, and U.S. Pat. No. 4,857,067, entitled "Disposable Diaper Having Shirred Ears," which issued on Aug. 15, 1989, to Wood, et al., describes a disposable diaper with elastic side panels that are intended to overlie the hips of the wearer. Those elastic structural elements are intended to permit expansion and contraction of the article in response to the wearer's motions and to maintain the fit of the absorbent article about the wearer during use.

A number of improvements to the basic Duncan et al. structure have been developed over the years. Some of those improvements have been directed to providing a better fit of the article on the body of the wearer and to reducing the likelihood of leakage of discharged materials between the absorbent article and the legs of the wearer. Accordingly, such absorbent articles have been provided with elastic leg openings, elastic waist elements, and elasticized side panels for improved fit. In that regard, one such improvement that has also achieved wide acceptance and substantial commercial success is an elasticized leg cuff structure that is disclosed in U.S. Pat. No. 3,860,003, entitled "Contractable Side Portions For Disposable Diaper", which issued on Jan. 14, 1975, to Buell.

Although several structural modifications and other changes for improving the fit and for reducing the incidence of leakage with such articles have been developed, those problems have not been fully solved. For example, it has been found that absorbent articles having elastic closures still often have a tendency to gap away from the body of the wearer during use. Those continuing problems have been found to be caused largely by the motions of the wearer during use of the article. Thus, as the wearer changes position, there can be significant dimensional changes in the wearer's waist, stomach, hips, buttocks, and legs. Such dimensional changes are particularly noticeable in infants. The circumference of the infant from hip to hip through the buttocks is much bigger than through the front waist and stomach area. Thus, as the wearer moves, the articles often are unable to expand and contract in proportion to the circumference of the wearer in the hips through the buttocks, caused primarily by their construction using materials that are relatively unaccomodating to such body changes by virtue of being made from relatively inelastic materials. Thus, the article tends to sag, to gap, and to slip to a degree that fit is degraded and the likelihood of leakage is increased. Further, because the article often cannot expand sufficiently to accommodate wide ranges of dimensional changes, the result is pressure that is applied to the body that can cause skin marking and wearer discomfort.

Thus, it would be advantageous to provide an absorbent article having elastic features that provide better fit. It would also be desirable to provide an absorbent article having improved dynamic fit relative to the body of the wearer, particularly in the waist and high areas. Further, it would be desirable to provide an absorbent article having a structure that more closely adapts to the dimensional changes in the wearer's body resulting from wearer movements. It would also be advantageous to provide an absorbent article with side panels with a structure that reduces or changes the tensile forces within the side panel to improve the fit of the article.

SUMMARY OF THE INVENTION

In accordance with one aspect of the present invention, there is provided an absorbent article that is worn about the waist and lower torso. The article is configured to be worn over and about the lower torso of a wearer. The article includes a containment assembly having a first longitudinal edge and a second longitudinal edge opposed thereof. The article further includes a first end edge and a second end edge opposed thereof. The first and the second longitudinal edges are configured to contact the legs of the wearer, and the first and the second end edges are configured to contact the waist of the wearer. The absorbent article further includes at least one side panel carried by the containment assembly and extending outwardly from the first longitudinal edge of the containment assembly adjacent the first end edge of the containment assembly. The side panel includes an inner region having at least one discontinuity for dividing a tensile force applied to the side panel into a waist-directing force and a leg-directing force. The side panel further includes a waist region and a leg region separated thereof by the at least one discontinuity. The waist region is configured to transmit the waist-directing force, and the leg region is configured to transmit the leg-directing force.

DETAILED DESCRIPTION OF THE INVENTION

As used herein, the term "absorbent article" refers to articles that are worn and that absorb and contain body exudates. More specifically, it refers to articles that are placed against or in close proximity to the body of the wearer to absorb and contain the various exudates discharged from the body.

The term "disposable" is used herein to describe absorbent articles that are not intended to be laundered or otherwise restored or reused as an absorbent article (i.e., they are intended to be discarded after a single use and, preferably, to be recycled, composted or otherwise disposed of in an environmentally compatible manner).

The term "unitary" as applied to an "absorbent article" refers to absorbent articles formed of separate parts that are joined together to form a coordinated entity so that they do not require separate manipulative parts like a separate holder and liner. One embodiment of a unitary absorbent article in accordance with the present invention is the disposable diaper 20 shown in FIG. 1.

As used herein, the term "diaper" refers to an absorbent article of the type generally worn by infants and other incontinent persons, and that is worn about the lower torso of the wearer. It should be understood, however, that the present invention is also applicable to other forms of absorbent articles, such as incontinent briefs, incontinent undergarments, diaper holders and liners, feminine hygiene garments, training pants, and the like.

Figure 1:
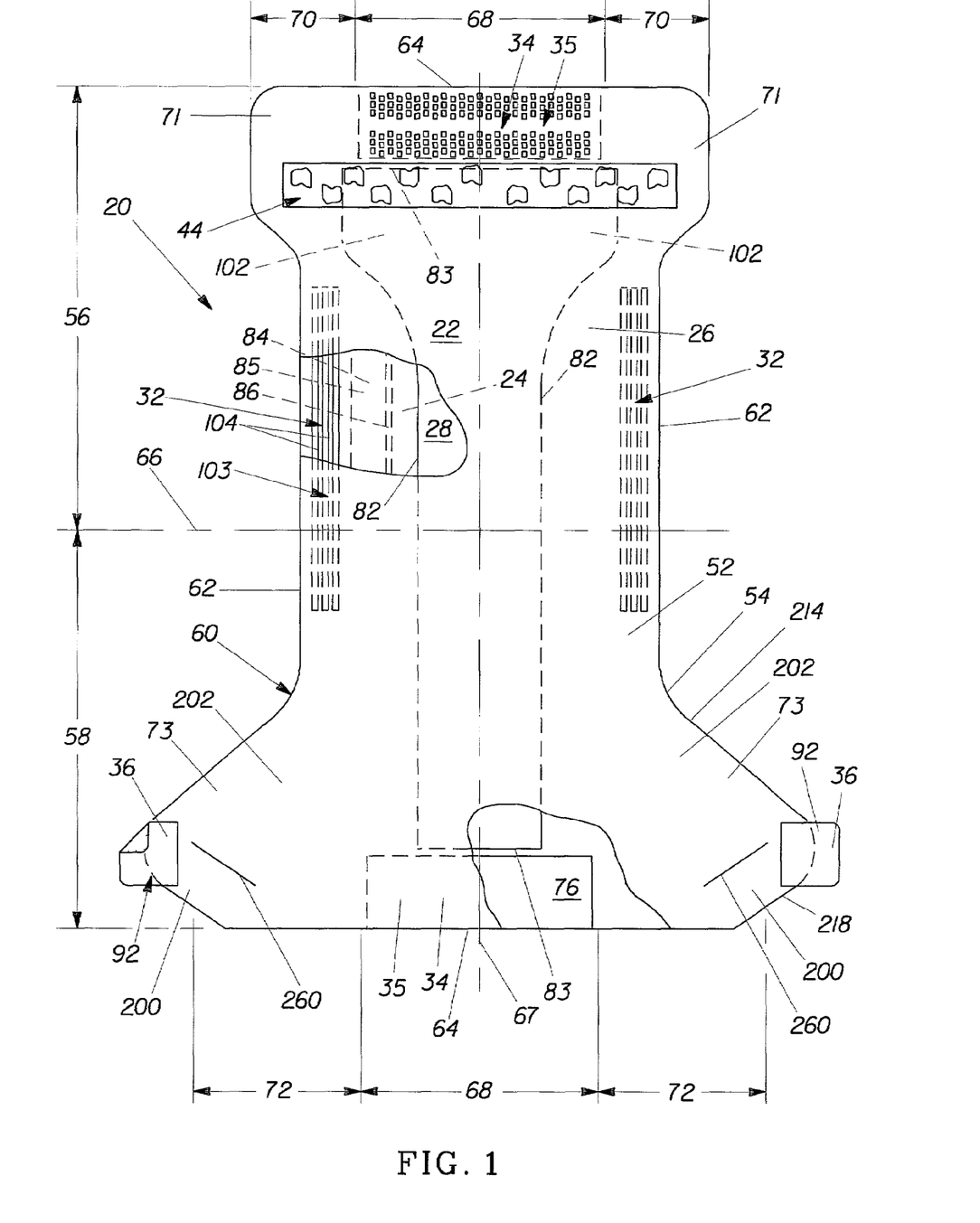
FIG. 1 is a plan view of one embodiment of the absorbent article of the present invention in the form of a disposable diaper having portions of the structure cut away to reveal underlying structure.

FIG. 1 is a plan view of a diaper 20 in accordance with the present invention. Diaper 20 includes several elasticized portions, some of which are normally in at least a partially contracted state so that part of the diaper includes gathered areas. As shown in FIG. 1, however, diaper 20 is in its flat-out, uncontracted state in which elasticized portions that are normally in at least partially contracted form and include some gathers when the diaper is in its initial condition, before it is applied to a wearer, have been stretched so that any elastic-induced initial contractions or gathers are overcome so that the diaper is shown in substantially completely flat condition. Elasticized portions that are normally in uncontracted, relaxed form before use, such as the side panels, are left in their uncontracted condition. As diaper 20 is illustrated in FIG. 1, outer surface 52, the portion of the diaper that faces away from the wearer when the diaper is worn, is facing the viewer of that drawing Figure. Additionally, portions of outer surface 52 of diaper 20 have been cut away to more clearly show the interior construction of the diaper.

As shown in FIG. 1, diaper 20 has containment assembly 22 that includes inner surface 54 that faces the body of the wearer when the diaper is worn. Preferably inner surface 54 is defined by liquid pervious topsheet 24. Diaper 20 also includes liquid impervious backsheet 26 that defines outer surface 52 and that is joined with topsheet 24 about their respective marginal edges, and absorbent core 28 positioned between topsheet 24 and backsheet 26. Additionally, for improved fit on the body of a wearer, diaper 20 also preferably includes elasticized leg cuffs 32, elasticized waist area 34, and side panels 73. Fastening elements defining fastening arrangement 36 are provided to secure the diaper in position on the body of the wearer.

Diaper 20 also includes front region 56, back region 58, and periphery 60 that are defined by the joined outer edges of each of topsheet 24 and backsheet 26. The longitudinal edges of the diaper 20 are designated 62 and the end edges are designated 64. Inner surface 54 of diaper 20 includes that portion of the diaper that is positioned adjacent to the wearer's body during use (i.e., inner surface 54 generally is formed by at least a portion of topsheet 24 and other components that can be joined to topsheet 24). Outer surface 52 of diaper 20 includes that portion of the diaper that is positioned away from the wearer's body (i.e., outer surface 52 generally is formed by at least a portion of backsheet 26 and other components that can be joined to backsheet 26). As used herein, the term "joined" includes directly securing one element to another element by affixing the elements directly to each other, either fully or partially, and it also includes indirectly securing one element to another element by affixing one element to one or more intermediate members that, in turn, can be affixed to the other element.

Front region 56 and back region 58 each extend from respective end edges 64 of diaper 20 inwardly to lateral centerline 66. Front region 56 includes central region 68 and a pair of end regions 70. Back region 58 includes central region 68 and a pair of end regions 72 that include laterally-outwardly-extending side panels 73. Although it is not essential that the side panels 73 be identical, they preferably are mirror images one of the other.

Containment assembly 22 of diaper 20 as shown in FIG. 1 defines the main body (chassis) of diaper 20 and is constructed to receive and retain the body exudates of the wearer. Containment assembly 22 includes at least absorbent core 28 and preferably outer covering layers, including topsheet 24 and backsheet 26, that enclose absorbent core 28. When the absorbent article includes both an exudate retainer and a separate liner, the containment assembly 22 generally includes the exudate retainer and the liner (i.e., containment assembly 22 includes one or more layers of material to define the exudate retainer, while the liner includes the topsheet and the backsheet.) For unitary absorbent articles, containment assembly 22 includes the main structure of the diaper with additional structural and functional elements added to form the composite diaper structure. Thus, containment assembly 22 for diaper 20 generally includes topsheet 24, backsheet 26, and absorbent core 28.

Topsheet 24 and backsheet 26 have length and width dimensions generally larger than those of absorbent core 28 and extend beyond the edges of absorbent core 28 to define periphery 60 of diaper 20. Although topsheet 24, backsheet 26, and absorbent core 28 can be assembled in a variety of well-known configurations, preferred diaper configurations are described generally in U.S. Pat. No. 3,860,003, entitled "Contractible Side Portions for Disposable Diaper," which issued on Jan. 14, 1975, to Kenneth B. Buell, and in U.S. Pat. No. 5,151,092, entitled "Absorbent Article With Dynamic Elastic Waist Feature Having A Predisposed Resilient Flexural Hinge," which issued on Sep. 29, 1992, to Kenneth B. Buell et al, the disclosure of each of the patents is hereby incorporated herein by reference.

Absorbent core 28 may comprise any absorbent material which is generally compressible, conformable, non-irritating to the wearer's skin, and capable of absorbing and retaining liquids such as urine and other certain body exudates. Absorbent core 28 may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles, such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

Backsheet 26, or any portion thereof, may be elastically extensible in one or more directions. In one embodiment, backsheet 26 may comprise a structural-elastic-like-film ("SELF") web. A SELF web is an extensible material that exhibits elastic-like behavior in the direction of elongation without the use of added elastic materials, and is described in more detail in U.S. Pat. No. 5,518,801 entitled "Web Materials Exhibiting Elastic-Like Behavior" issued to Chappell, et al. on May 21, 1996, and which is incorporated herein by reference. In alternate embodiments, the backsheet 26 may comprise elastomeric films, foams, strands, or combinations of these or other suitable materials with nonwovens or synthetic films.

Topsheet 24 is preferably compliant, soft-feeling, and non-irritating to the wearer's skin. Topsheet 24 may comprise one or more apertures to ease penetration of exudates therethrough, such as urine and/or feces (solid, semi-solid, or liquid). The size of at least the primary aperture is important in achieving the desired waste encapsulation performance. If the primary aperture is too small, the waste may not pass through the aperture, either due to poor alignment of the waste source and the aperture location or due to fecal masses having a diameter greater than the aperture. If the aperture is too large, the area of skin that may be contaminated by "rewet" from the article is increased. Typically, the aperture should have an area of between about 10 $cm^2$ and about 50 $cm^2$. The aperture preferably has an area of between about 15 $cm^2$ and 35 $cm^2$.

Diaper 20 preferably further includes leg cuffs 32 which provide improved containment of liquids and other body exudates. Leg cuffs 32 may also be referred to as leg bands, side flaps, barrier cuffs, or elastic cuffs. U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. on Feb. 28, 1989 and Mar. 20, 1990, respectively, describe disposable diapers having "stand-up" elasticized flaps (barrier cuffs) which improve the containment of the leg regions. U.S. Pat. Nos. 4,695,278 and 4,795,454 issued to Lawson on Sep. 22, 1987 and to Dragoo on Jan. 3, 1989, respectively, describe disposable diapers having dual cuffs, including gasketing cuffs and barrier cuffs. In some embodiments, it may be desirable to treat all or a portion of leg cuffs 32 with a lotion, as described above. The disclosures of each of those patents are hereby incorporated by reference.

Although each leg cuff 32 can, if desired, be configured to be similar to any of the leg bands, side flaps, barrier cuffs, or elastic cuffs described in the patents identified above, it is preferred that each leg cuff 32 includes gasketing cuff 103 and barrier cuff 84, such as that described in the above-identified U.S. Pat. Nos. 4,695,278 and 4,795,454. As shown in FIG. 1, gasketing cuff 103 includes a portion of topsheet 24, a portion of backsheet 26, and a plurality of elastic members 104 positioned therebetween, while barrier 84 includes a barrier flap 85 and one or more spacing elastic members 86.

The diaper 20 preferably further includes elastic waist feature 34 that provides improved fit and containment. Elastic waist feature 34 is that portion or zone of the diaper 20 that is intended to elastically expand and contract to dynamically fit the wearer's waist. Elastic waist feature 34 at least extends longitudinally outwardly from at least one of waist edges 83 of absorbent core 28 and generally forms at least a portion of end edge 64 of diaper 20. Disposable diapers are generally constructed so as to have two elastic waist features, one positioned in the front region and one positioned in the back region, although diapers can instead be constructed with a single elastic waist feature. Further, while the elastic waist feature or any of its constituent elements can include a separate element affixed to the diaper, elastic waist feature 34 is preferably constructed as an extension of other elements of the diaper 20, such as backsheet 26 or topsheet 24, preferably both backsheet 26 and topsheet 24. As shown in FIG. 1, elastic waist feature 34 includes elasticized waistband 35 that at least includes elastic waist member 76, which may include a crosslinked natural rubber foam, operatively associated between topsheet 24 and backsheet 26. Elastic waist feature 34 may be constructed in a number of different configurations including those described in U.S. Pat. No. 4,515,595 issued to Kievit et al. on May 7, 1985; U.S. Pat. No. 4,710,189 issued to Lash on Dec. 1, 1987; U.S. Pat. No. 5,151,092 issued to Buell on Sep. 9, 1992; and U.S. Pat. No. 5,221,274 issued to Buell on Jun. 22, 1993. Other suitable waist configurations may include waistcap features such as those described in U.S. Pat. No. 5,026,364 issued to Robertson on Jun. 25, 1991 and U.S. Pat. No. 4,816,025 issued to Foreman on Mar. 28, 1989. The disclosure of each of those references is hereby incorporated herein by reference.

The diaper 20 may also include a fastening system 36. The fastening system 36 preferably maintains the front region 56 and the back region 58 in a configuration so as to provide lateral tensions about the circumference of the diaper 20 to hold the diaper 20 on the wearer. The fastening system 36 preferably comprises a surface fastener such as tape tabs 92, hook and loop fastening components and/or hermaphroditic fastening components, although any other known fastening means are generally acceptable. Some exemplary surface fastening systems are disclosed in U.S. Pat. No. 3,848,594 entitled "Tape Fastening System for Disposable Diaper" issued to Buell on Nov. 19, 1974; U.S. Pat. No. B1 4,662, 875 entitled "Absorbent Article" issued to Hirotsu et al. on May 5, 1987; U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946, 527 entitled "Pressure-Sensitive Adhesive Fastener And Method of Making Same" issued to Battrell on Aug. 7, 1990; the herein before referenced U.S. Pat. No. 5,151,092 issued to Buell on Sep. 9, 1992; and U.S. Pat. No. 5,221,274 issued to Buell on Jun. 22, 1993. An exemplary interlocking fastening system is disclosed in co-pending U.S. application Ser. No. 09/143,184 entitled "Absorbent Article Fastening Device" in the names of Kline et al. filed on Aug. 8, 1998. The fastening system 36 may also provide a means for holding the article in a disposal configuration as disclosed in U.S. Pat. No. 4,963,140 issued to Robertson et al. on Oct. 16, 1990. The fastening system may also include primary and secondary fastening systems, as disclosed in U.S. Pat. No. 4,699,622 entitled "Disposable Diaper Having An Improved Side Closure" issued to Toussant et al. on Oct. 13, 1987 to reduce shifting of overlapped portions or to improve fit as disclosed in U.S. Pat. No. 5,242,436 entitled "Absorbent Article With Fastening System Providing Dynamic Elasticized Waistband Fit" issued to Weil et al. on Sep. 7, 1993; U.S. Pat. No. 5,499,978 entitled "Absorbent Article With Dynamic Elastic Waist Feature Having A Predisposed Resilient Flexural Hinge" issued to Buell et al. on Mar. 19, 1996; U.S. Pat. No. 5,507,736 entitled "Absorbent Article With Dynamic Elastic Waist Feature Comprising An Expansive Tummy Panel" issued to Clear et al. on Apr. 16, 1996; U.S. Pat. No. 5,591,152 entitled "Absorbent Article With Dynamic Elastic Waist Feature Having A Predisposed Resilient Flexural Hinge" issued to Buell et al. on Jan. 7, 1997. Each of these patents and the co-pending application are incorporated herein by reference. In alternative embodiments, opposing sides of the article may be seamed or welded to form a pant. This allows the article to be used as a pull-on type diaper, such as a training pant.

Diaper 20 may also includes at least one, but preferably two side panels 73 positioned preferably in back region 58 for connecting waist features 34 of diaper 20 around the wearer. Alternatively, if desired, the side panel 73 can instead be positioned in the front of the wearer, adjacent the stomach of the wearer, if desired.

Side panel 73 can be secured to the containment assembly 22 by any suitable method, including by a suitable adhesive, by heat sealing, by ultrasonic sealing, by pressure bonding, or combinations thereof. In that regard, the proximal region 214 of the side panel 73 can be secured to topsheet 24, or to backsheet 26, or to any layer of material disposed between backsheet 24 and topsheet 26, if desired. Alternatively, if desired, side panel 73 can be integrally formed with topsheet 24 and/or backsheet 26 or any one or more layers of materials joined to topsheet 24 and/or backsheet 26.

Side panels 73 can take on a number of different sizes, shapes, configurations and materials. The exact length, width, and thickness of side panel 73 can vary depending on the dimensions of the intended user and the exact configuration of side panel 73. Examples of the size of suitable side panels 73 to be part of a diaper 20 worn by a medium sized infant are that they be generally trapezoidal in shape, having dimensions between about 2 and 4 inches in the longitudinal direction of diaper 20 and between about 2 and 5 inches in the lateral direction of diaper 20. It should be noted that although shown as defined by substantially straight lines, each of the peripheral edges of side panel 73 can be defined by curved lines, if desired, or by a combination of straight and curved lines.

Each of side panels 73 can be formed from any suitable extensible, stretchable, or elastomeric material. (As used herein, the term "extensible" refers to materials that can increase in at least one dimension. The term "stretchable" refers to materials that are extensible when stretching forces are applied to the material, and offer some resistance to extension. The term "elastomeric" refers to materials that extend in at least one direction when a force is applied and return to approximately their original dimensions after the force is released.) The extensible, stretchable, or elastomeric material can include a single layer material or a laminate of two or more layers of materials that have been joined together. One material that has been found to be especially suitable for use in side panels 73 is a laminate of two coverstock layers with an elastomeric film sandwiched between the coverstock layers. As used herein "coverstock" can include any woven or nonwoven materials. An example of a suitable coverstock material is a nonwoven material manufactured by Veratec, Inc., a Division of the International Paper Company, of Walpole, Mass., designated P-8. An example of a suitable film to be sandwiched between coverstock layers is the elastomeric film EXX-500, (formerly EXX-7) manufactured by the Exxon Chemical Company of Lake Zurich, Ill. Other suitable materials for use as, or in the extensible side panels and side panel members include structural, elastic-like film (SELF) webs, as described hereinbelow, synthetic or natural rubber, synthetic or natural rubber foams, elastomeric scrims, woven or nonwoven elastomeric webs, elastomeric composites such as elastomeric nonwoven laminates, zero strain stretch laminates, prestrained stretch laminates or the like. U.S. Pat. No. 5,151,092, entitled "Absorbent Article with Dynamic Elastic Waist Feature Having a Predisposed Resilient Flexural Hinge," which issued on Sep. 29, 1992, to Buell et al., describes suitable zero stain stretch laminates and prestrained stretch laminates, and the disclosure of that patent is hereby incorporated herein by reference to the same extent as if fully rewritten.

One preferred mechanical operation suitable for providing stretch characteristics in a material to be used for the side panels is described hereinabove with respect to imparting elasticity to backsheet 24. As described hereinabove, structural elastic-like film (SELF) web is an extensible material that exhibits an elastic-like behavior in the direction of elongation without the use of added elastic materials. Methods and apparatus for forming such SELF webs are disclosed in U.S. Pat. No. 5,156,793, entitled, "Method for Incrementally Stretching Zero Strain Stretch Laminate Sheet in a Non-Uniform Manner to Impart a Varying Degree of Elasticity Thereto," which issued on Oct. 20, 1992, to Kenneth B. Buell et al.; in U.S. Pat. No. 5,167,897, entitled, "Method for Incrementally Stretching a Zero Strain Stretch Laminate Sheet to Impart Elasticity Thereto," which issued on Dec. 1, 1992, to Gerald M. Weber et al.; and in U.S. Pat. No. 5,518,801, entitled, "Sheet Materials Exhibiting Elastic-Like Behavior," which issued on May 21, 1996, to Charles W. Chappell et al., the disclosures of each of the patents is hereby incorporated herein by reference to the same extent as if fully rewritten.

The strainable web material can be used in various different forms in extensible side panels 73 of diaper 20. One example of a suitable form of structural elastic-like film is a laminate. The laminate includes a strainable web material secured between two longitudinally extensible, preferably carded, nonwoven webs. (In addition, the strainable web material can also be used in the various other components of the absorbent article described herein.)

Alternatively, side panels 73 can be made from extensible materials having areas of different elastic behavior achieved by means other than the aforementioned mechanical operations, such as slitting or cutting the extensible material that forms the side panels 73. In such embodiments, the slits or cuts in the material are not limited to any particular sizes or shapes. For example, the material making up the side panels 73 can be fully or partially severed or can have portions cut out or bonded to create different extensibility characteristics in the side panels.

As used herein, the term "fully severed" refers to single component side panels having a cut or slit running the entire distance between the proximal edge to the distal edge of the extensible side panel. The term "partially severed" refers to single component side panels having a cut or slit that does not extend from the proximal edge to the distal edge of the side panels.

Figure 2:
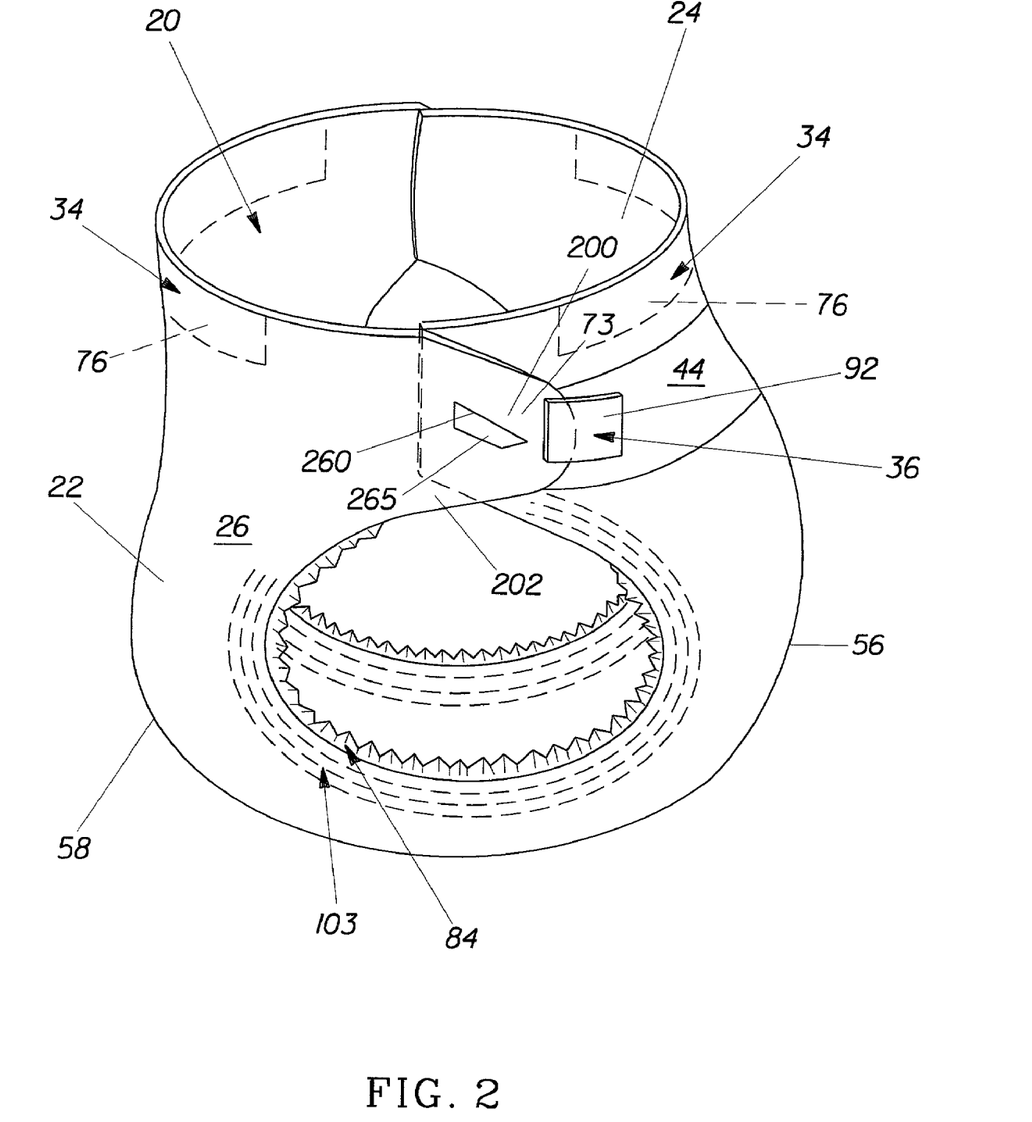
FIG. 2 is a perspective view of one embodiment of the absorbent article of the present invention in its assembled form when worn.

FIG. 2 illustrates diaper 20 in its assembled form, after application of diaper 20 to the body of a wearer. Diaper 20 may be applied to a wearer by positioning back region 58 under the wearer's lower back and by drawing the remainder of the diaper between the wearer's legs so that front region 56 is positioned over the abdomen of the wearer. The tab portions of tabs 92 are then released to expose the adhesive, and the person applying the diaper then individually draws each of side panels 73 around the waist of the wearer, while still grasping tab 92. Side panels 73 will typically be under tension and will be at least partially extended during that application operation, to conform diaper 20 with the size and shape of the wearer. Fastening component of tabs 92 are then individually attached to effect the side closure of diaper 20 and to secure diaper 20 about the lower torso of the wearer.

Referring to FIGS. 1 and 2 showing one embodiment of the present invention, wherein side panel 73 includes cut line 260 which separates the force-transmitting capability of side panels 73 into a pair of distinct regions, waist region 200 and leg region 202. (Cut line 260 can severe the side panel material through the side panel material, or partially, severing any one or more layers of the side panel material leaving one or more layers uncut. As shown in FIG. 2, the tension applied to side panel 73 may cause the edges of cut line 260 to separate to define opening 265.) Waist region 200 and leg region 202 can function substantially independently of each other and can sustain and transmit different levels of tensile forces to different portions of the diaper structure. Waist regions 200 and leg region 202 extend preferably outwardly from diaper 20 at different angles, relative to transverse centerline 66, to meet and connect with each other at an area adjacent to tab 92. Because regions 200 and 202 diverge from each, waist region 200 has a different primary direction of extensibility than does leg region 202, which provides side panel 73 with unique, multi-directional stretch characteristics. Thus, when waist region 200 is placed under tension, by pulling laterally outwardly on tab 92, the tensile force within waist region 200 is transmitted to and acts on elastic waist feature 34 of diaper 20 to impart a tensile force to elastic waist feature 34 that serves to maintain tension within the elastic waist feature 34 to retain diaper 20 in a predetermined position about the wearer's waist. Because both side panels 73 and elastic waist feature 34 may be extensible, they each can expand and contract in response to body dimensional changes resulting from movements of the wearer, and thereby serve to maintain elastic waist feature 34 of diaper 20 in a snug, yet comfortable, fit against the wearer's body throughout the period of use of the diaper. Thus, diaper 20 is retained in its proper operative position on the body of the wearer so that diaper 20 is effective for its intended purpose.

Similarly, when leg region 202 is placed under tension, which also results from pulling laterally outwardly on tab 92, the tensile force within leg region 202 is transmitted to and acts on elasticized cuff 32 of diaper 20. As a result, leg cuff 32 is maintained under tension so that it remains in close contact about the wearer's thigh to prevent leakage between the diaper and the wearer's thigh. Because side panel 73 and leg cuff 32 each may be extensible, they each can expand and contract in response to body dimensional changes resulting from movements of the wearer, and they thereby serve to maintain leg cuff 32 in snug, yet comfortable, contact with the wearer's thigh throughout the period of use of diaper 20 to prevent leakage between cuff 32 and the wearer's thigh.

Figure 3:
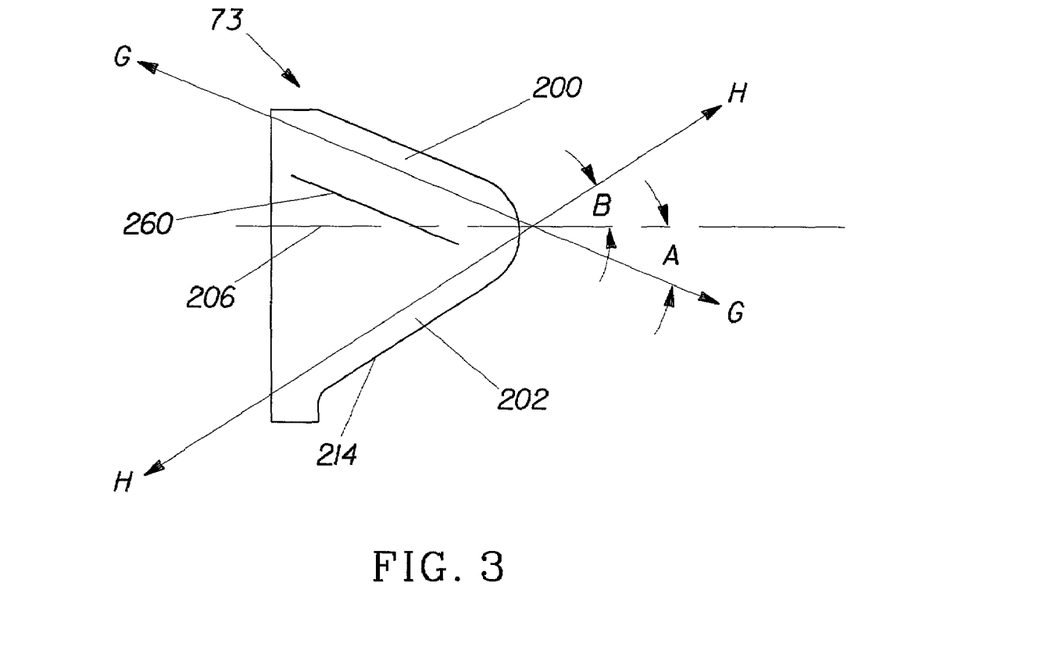
FIG. 3 is a diagrammatic view showing the tensile force vectors in a side panel of the absorbent article of the present invention of FIGS. 1 and 2.

Referring to FIG. 3 showing an enlarged view of side panel 73 of FIG. 1, wherein because of the position of cut line 260, waist region 200 has a primary direction of extensibility G—G that is different from a primary direction of extensibility H—H of leg region 202, thereby providing side panel 73 with unique multi-directional stretch characteristics. Waist region 200 is that portion or element of side panel 73 designed to initially provide the tension to secure diaper 20 about the waist of the wearer, and once "activated", or made extensible, to thereafter dynamically expand and contract with the motions of the wearer to maintain the waist of the diaper in a snug yet comfortable fit throughout the period of use. Preferably, waist region 200 is positioned so that first lateral edge 218 is positioned to connect with and to form a part of end edge 64 of diaper 20.

The primary direction of extensibility G—G of waist region 200 includes a first vector component oriented laterally outwardly that is preferably greater than zero, and a second vector component that is preferably greater than or equal to zero and is oriented toward lateral centerline 66 of diaper 20. More preferably, the first vector component of the primary direction of extensibility G—G is greater than the second vector component. (It should be noted, however, that the whole or segments of the waist region 200 can also be extensible in directions other than the primary direction of extensibility G—G.) An angle A in FIG. 3 represents the angle (measured clockwise or counterclockwise) between the primary direction of extensibility G—G of waist panel 200 and side panel lateral axis 206, which is generally parallel to lateral centerline 66. (In FIG. 3, angle A is measured in a clockwise direction from lateral axis 206.) Angle A can vary from about 0° to about 45° or from about 5° to about 20° or from about 10° to about 15°.

Leg region 202 is that portion or element of side panel 73 intended to expand and contract with the dynamic motions of the wearer in the outer thigh region, where the diaper encircles the wearer's leg. As shown in FIG. 3, leg region 202 has a second lateral edge 214. Preferably, leg region 202 is disposed adjacent longitudinal edge 62 of diaper 20 and extends laterally outwardly from a location closer to transverse centerline 66 of diaper 20 than does waist region 200. Preferably, when diaper 20 is fitted to the wearer, second lateral edge 214 forms a part of the diaper 20 that encircles the thigh of the wearer.

The primary direction of extensibility H—H of leg region 202 includes a first vector component oriented laterally outwardly that is preferably greater than zero, and a second vector component that is preferably greater than or equal to zero and is oriented away from the lateral centerline 66. (The whole or segments of region 202 can also be made to be extensible in directions other than the primary direction of extensibility, if desired.) As shown in FIG. 3, angle B represents the angle between the primary direction of extensibility H—H of leg region 202 and side panel lateral axis 206. (As used herein, the angle B is measured counterclockwise from lateral axis 206.) Angle B can vary from about 0 and to 40 degrees or from about 10 to about 35 degrees or from about 20 to about 30 degrees. In one preferred embodiment, when diaper 20 is initially fitted to the wearer, leg region 202 overlies the outer thigh portion of the wearer's leg. Once made extensible, leg panel 202 is capable of expansion and contraction in response to the motions of the wearer's legs to maintain a snug fit of leg cuff 32 about the leg of the wearer throughout the period of use of the diaper. This improves the containment characteristics of the diaper while also reducing the likelihood of red marks on the wearer's skin from excessive leg cuff tension.

Each of regions 200 and 202 can take on a number of different sizes, shapes, configurations and materials. The exact length, width, and thickness of waist region 200 and leg region 202, will vary depending on the dimensions of the intended user and the exact configuration of side panel 73. Accordingly, waist region 200 can be identical in size and shape with leg region 202, or it can have different dimensions, so long as waist region 200 can be operatively associated with leg region 202 and containment assembly 22 of diaper 20 to provide the multi-directional stretch characteristics of the invention described herein.

Figure 4:
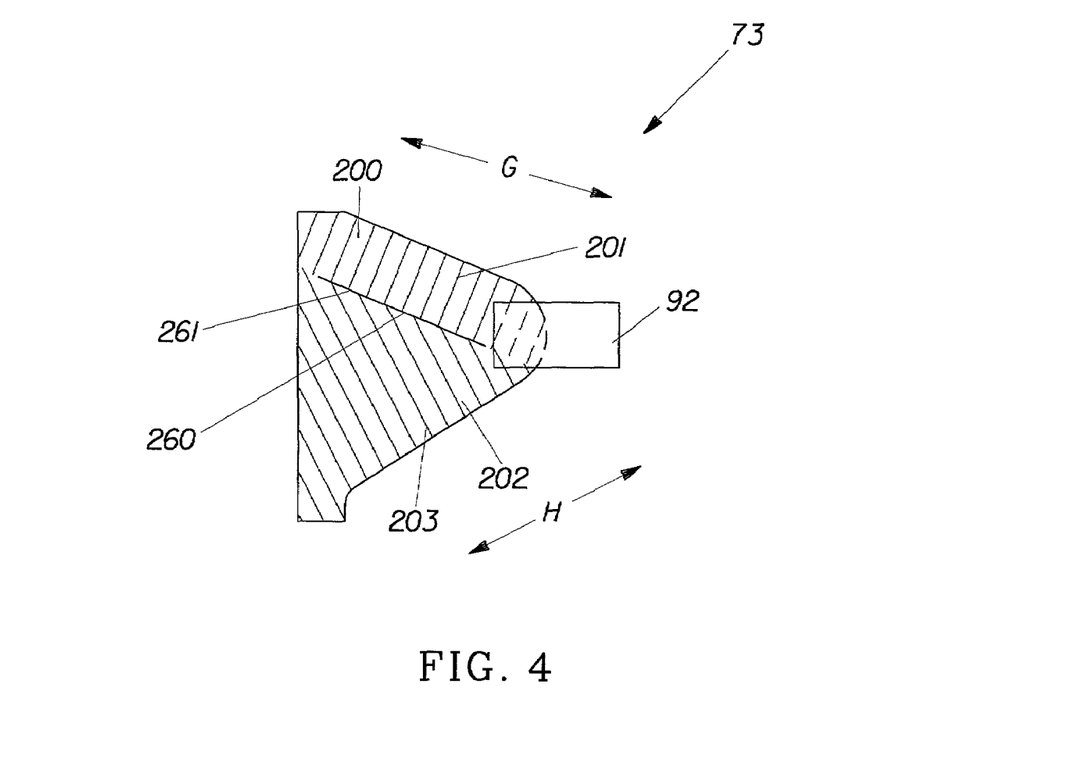
FIG. 4 is another diagrammatic view showing a side panel of the present invention that includes extensibility patterns.

In one preferred embodiment as shown in FIG. 4, waist region 200 preferably has a primary direction of extensibility G—G that is substantially parallel with first lateral edge 218 of side panel 73. Lines 201 represent the axes of one preferred SELFing pattern in waist region 200, and are disposed preferably generally perpendicular to primary direction of extensibility G—G. Leg region 202 preferably has a primary direction of extensibility H—H at an angle to the lateral centerline 66 and the longitudinal centerline 67 of diaper 20 and that is preferably generally parallel with second lateral edge 214 of side panel 73. Lines 203 represent the axes of one preferred SELFing pattern in leg region 202, and are disposed substantially perpendicular to primary direction of extensibility H—H. The embodiment of side panel 73 shown in FIG. 4 is a single-piece side panel having a distinct boundary line 261 between the waist region 200 and leg region 202 that defines where the elastic characteristics of each region begins and ends. Boundary line 261 is preferably aligned with cut line 260. If desired, boundary line 261 between waist region 200 and leg region 202 can be located at other positions on side panel 73.

Figure 5:
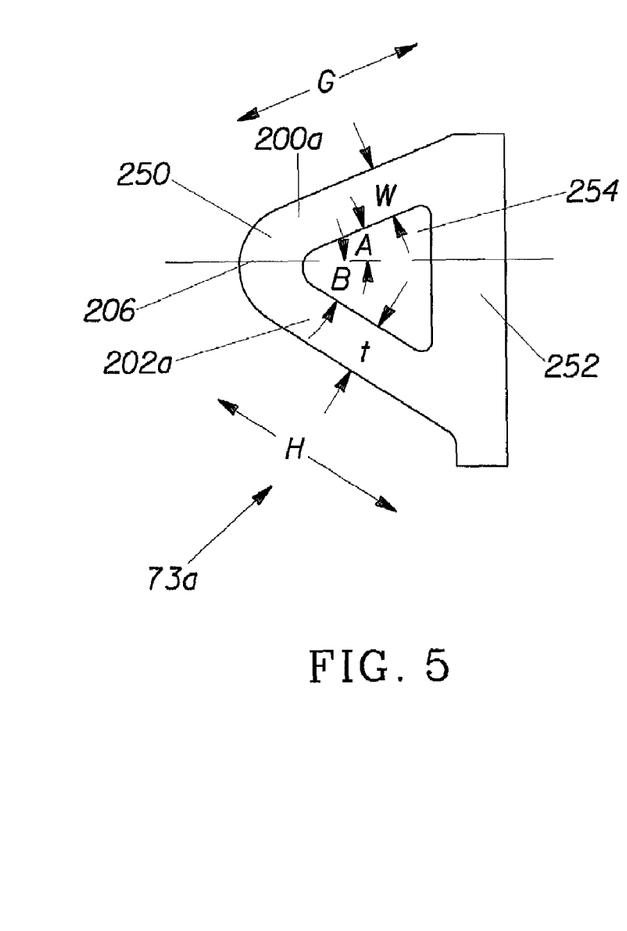
FIG. 5 is another diagrammatic view of a side panel of the present invention having one form of interiorly-positioned opening.

Referring to FIG. 5, there is shown another embodiment of a single piece, or unitary, side panel 73a. As shown, side panel 73a can have outer panel 250 and inner panel 252, wherein outer panel 250 has a shorter length, taken in the longitudinal direction of diaper 20, than does inner panel 252. In that regard, inner panel 252 can serve as a connector joined to assembly 22 by a suitable adhesive, by heat sealing, by ultrasonic sealing, by pressure bonding or any combination thereof. Alternatively, side panel 73a can be integrally formed with backsheet 24 and/or with topsheet 26, if desired.

Extending between outer panel 250 and inner panel 252 are waist panel 200a and leg panel 202a, each of which is disposed preferably angularly relative to each of outer panel 250 and inner panel 252. Waist panel 200a can extend at an angle A relative to lateral axis 206 of side panel 73a, and leg panel 202a can extend at an angle B relative lateral axis 206 of side panel 73a. In that respect, as noted earlier in connection with FIG. 3, angle A preferably can vary from about 0° to about 45° or from about 5° to about 20° or from about 10° to about 15°, while angle B can vary from about 0° to about 40° or from about 10° to about 35° or from about 20° to about 30°. Waist panel 200a and/or leg panel 202 can have a SELF pattern arranged as shown, for example, in FIG. 4, wherein the individual SELF pattern lines for waist panel 200a are disposed at an angle relative to the individual SELF pattern lines for leg panel 202a.

Side panel 73a can include an interior open area 254 that is devoid of material. As shown, open area 254 can also be of generally trapezoidal form, but it can also be of triangular form, if desired, and it preferably includes stress-relieving corners that can either be chamfer-like, as shown, or, alternatively, they can be concavely curved, or they can be of any other convenient form that reduces the tendency for tearing to occur at the corners of open area 254 when side panel 73a is subjected to tensile stresses. Additionally, open area 254 is preferably positioned relative to the outer edges of side panel 73a as to define a waist panel 200a that has a width w that is preferably greater than the width t of leg panel 202a. Preferably, the ratio w/t can vary from about 1:1 to about 4:1 or from about 1.1:1 to about 3:1 or from about 1.25:1 to about 2:1, so that the tensile forces within waist panel 200a are generally greater than those within leg panel 202a. Moreover, the widths of each of regions 200a and 202a are preferably uniform along the lengths of the respective regions, as shown in FIG. 5, although the widths can vary or be different along the lengths of the respective regions, if desired.

Inner panel 252 is preferably joined to containment assembly 22 of diaper 20, preferably at waist feature 34 that is intended to be positioned at the back of the wearer when the diaper is worn, although it can instead be attached to the waist feature 34 adjacent the stomach of the wearer, if desired. Additionally, if desired, a suitable stiffener element can be attached to inner panel 252 along the inner side edge of the side panel to prevent or limit gathers or puckers in the side panel material and in the adjoining backsheet material when the side panel is placed under tension, such as while the article is being applied to the wearer and also while the article is worn.

Waist panel 200a preferably has an extensibility which can vary from about 5 g/mm to about 50 g/mm or from about 10 g/mm to about 40 g/mm or from about 15 g/mm to about 25 g/mm. If the extensibility is too high the effort required to tension side panel 73 is too large for convenience, and waist feature 34 of diaper 20 will exert too great a force against the wearer's stomach. In contrast, if the extensibility is too low, the holding force acting about the wearer's waist will also be too low. This may result in diaper 20 slipping down from the wearer's waist, thereby rendering diaper 20 ineffective for its intended use.

Leg panel 202a preferably has an extensibility which can vary from about 1 g/mm to about 30 g/mm or from about 3 g/mm to about 20 g/mm or from about 5 g/mm to about 15 g/mm. If the extensibility is too high, leg cuffs 32 will be under high tension, tending to cut into the wearer's thighs, leading to discomfort from excessive pressure of leg cuff 32 against the thigh and to resulting red marks. If the extensibility is too low, leg cuffs 32 might not be tensioned sufficiently to maintain complete contact of leg cuff 32 completely around the wearer's thigh. This may result in leakage between leg cuff 32 and the thigh.

Figure 6:
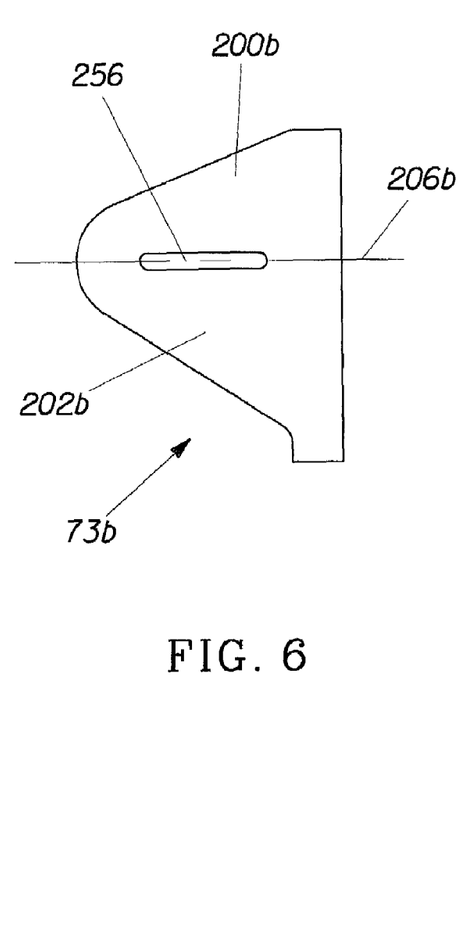
FIG. 6 is an alternative embodiment of the present invention showing a side panel with a differently-shaped interiorly-positioned opening.

Another form of an interior open area in side panel 73 to provide the benefits of the present invention is shown in FIG. 6, wherein an elongated, narrow open area 256 is provided in side panel 73b. Open area 256 includes substantially parallel sides and terminates in rounded corners to reduce stress concentrations and prevent tearing of side panel. The longitudinal centerline 206b of open area 256 extends preferably substantially perpendicular to longitudinal centerline 67 of diaper 20 and is preferably offset from the longitudinal centerline 206 of side panel 73b so that the waist panel 200b has a greater effective width than does the leg panel 202b. Other forms of interior open areas can also be provided, and they preferably are so formed and positioned to result in a larger tensile force in waist panel 200b than in leg panel 202b when side panel 73b is placed under tension by a tensile force applied to side panel 73b, such as during the time diaper 20 is being applied to a wearer and also when it is being worn.

Figure 7:
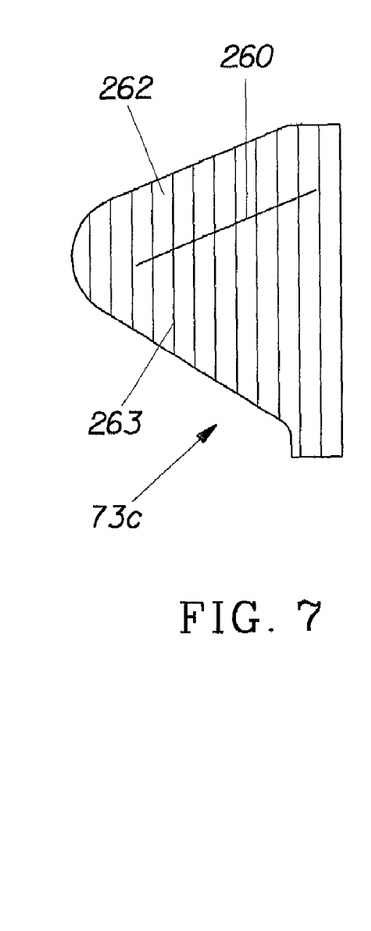
FIG. 7 is another embodiment of the present invention showing a side panel having a single, interiorly-positioned rectilinear slit.
Figure 8:
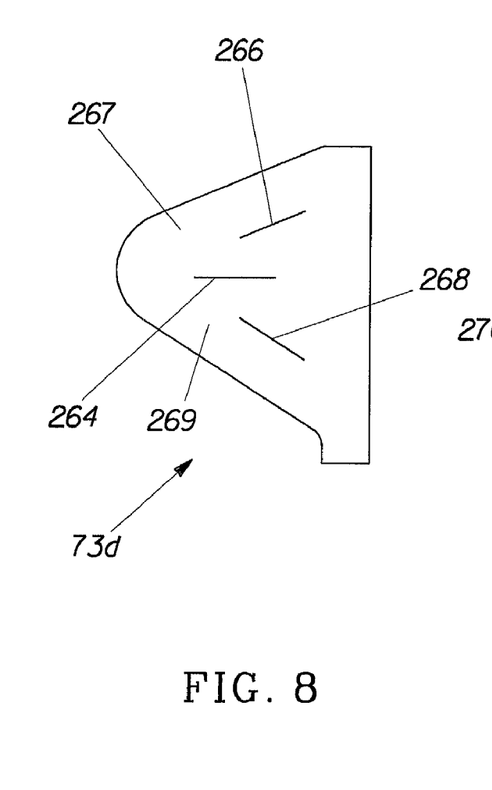
FIG. 8 is an alternative embodiment of a present invention showing a side panel having a plurality of interiorly-positioned, separated rectilinear slits.

In addition to interiorly-positioned open areas having the form illustrated in FIGS. 5 and 6, another way in which the relative levels of tensile forces within the side panel in the waist direction and in the leg-cuff direction can be controlled is by providing one or more cuts or slits extending through the side panel material. Referring to FIGS. 7 and 8, one or more rectilinear cuts or slits can be provided in the interior portion of the respective side panels shown. In the FIG. 7 embodiment, which shows side panel 73c, there is only a single slit 260, which extends in the direction of and defines the width of waist region 262, and which therefore defines the division of tensile forces between the waist region 262 of side panel 73c and a leg region 263. Slit 260 is inclined relative to lateral centerline 66 of diaper 20, preferably at angle A (see FIGS. 3 and 5 and accompanying description hereinabove), and preferably has a length which can vary from about 0.125 in (about 3 mm). to about 2.5 in. (about 64 mm) or about 0.25 in. (about 6 mm) to about 2.0 in. (about 50 mm) or from about 0.5 in. (about 13 mm) to about 1.5 in (about 38 mm).

FIG. 8 illustrates another embodiment of side panel 73d of the present invention having more than one slit, for example, three generally rectilinear slits 264, 266, and 268. Slit 264 can extend in a direction substantially perpendicular to longitudinal centerline 67 of diaper 20 and serves to divide the tensile force applied to side panel 73d between the waist region 267 and the leg region 269. Slit 266 can extend in the direction of and can define the width of waist region 267, and slit 268 can extend in the direction of and can define the width of leg region 269. The angular disposition of slits 266 and 268 can be within the ranges specified hereinabove for angles A and B, respectively, in connection with the discussion of FIG. 3. The lengths of slits 264, 266, and 268 can vary from about 0.125 in. (about 3 mm) to about 2.5 in. (about 64 mm) or from about 0.25 in. (about 6 mm) to about 2.0 in. (about 51 mm) or from about 0.5 in. (about 13 mm) to about 1.5 in (about 38 mm).

Figure 9:
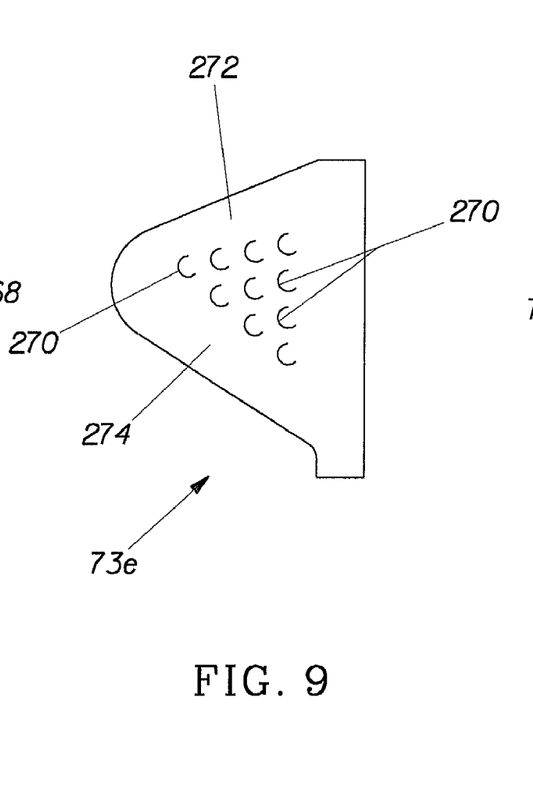
FIG. 9 is another embodiment of the present invention showing a side panel having a plurality of interiorly-positioned curvilinear slits.

Another embodiment of side panel 73e which also includes a plurality of slits, is shown in FIG. 9, wherein slits 270 are each preferably curvilinear, or arc-shaped, with the respective centers of arcs 270 positioned inwardly of arcs 270 so that the open portions of arcs 270 face toward longitudinal centerline 67 of diaper 20. Arcs 270 are so positioned relative to each other to define a generally triangular pattern of arcs 270, to divide a lateral tensile force applied to side panel 73e so that individual tensile forces are directed to waist region 272 and leg region 274 of side panel 73e. Arcs 270 can have the same size radii or they can have differently-sized radii. In that regard, arcs 270 have radii which can vary from about 1.0 in. (about 25 mm) to about 20 in. (about 508 mm) or from about 2.0 in. (about 51 mm) to about 15 in. (about 38 mm) or from about 5 in. (about 127 mm) to about 10 in. (about 254 mm).

The cuts and openings shown in FIGS. 4–9 operate as interiorly-positioned stress relief or stress interruption areas, and they preferably are so disposed as to cause the tensile forces applied to the respective side panels to be divided between the waist region and the leg region of the side panel, so that each of the diaper waist regions and the leg regions are under a tensile stress that serves to hold the diaper about the wearer's waist and about the wearer's thighs without unduly large hoop stresses within the diaper structure that could operate to cause discomfort to the wearer or red marks on the wearer's skin.

Figure 10:
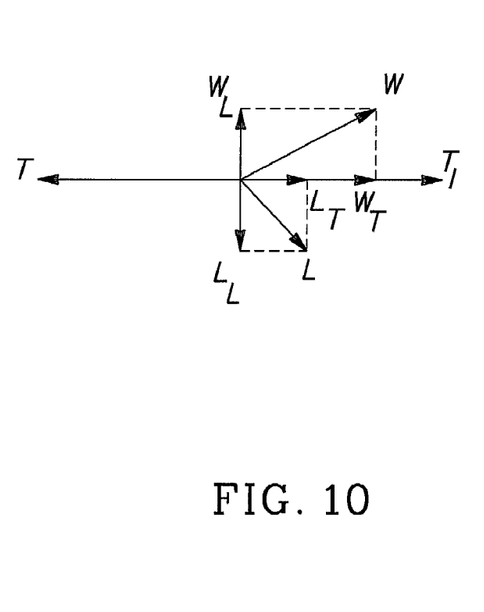
FIG. 10 is a force diagram showing the division of forces provided by a side panel in accordance with the present invention.

The force-dividing effect of the interior cuts and openings in the side panels is illustrated diagrammatically in FIG. 10. As noted earlier, interiorly-positioned openings and cuts in the material from which the side panels are formed serve to reduce or prevent the transmission of tensile forces within the side panels along the same line as that of an applied external tensile force. In that regard, the external tensile force T is divided into a waist-directed force W and a leg-cuff-directed force L. Because of the effect of the cuts and openings in reducing the transmission of tensile forces within the side panel in a direction opposite to and aligned with the direction of the externally-applied tensile force, the tensile forces within the side panel extend angularly relative to the externally-applied force. When resolved into their respective components, waist region force W has a longitudinal component $W_L$ that extends in the direction of the longitudinal axis 67 of diaper 20, and a transverse component $W_T$ that extends in the direction of the lateral centerline 66 of diaper 20. Similarly, leg region force L has a longitudinal component $L_L$ that extends in the direction of the longitudinal axis 67 of diaper 20, and a transverse component $L_T$ that extends in the direction of the lateral centerline 66 of diaper 20.

As the diaper 20 is applied to the wearer, each of the side panels is stretched laterally to place it under tension. When the diaper has been placed in position and secured, the diaper and its components are in equilibrium and $W_L=L_L$ and $W_T+L_T=T$. As will be appreciated by those skilled in the art, the division of tensile forces within the side panels can be varied to accommodate particular conditions. Accordingly, the sizes and orientations of interiorly-positioned openings and cuts can be varied to provide the desired results.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. A disposable article configured to be worn over and about the lower torso of a wearer, the article comprising:
  a) a containment assembly having a first longitudinal edge and a second longitudinal edge opposed thereto, a first end edge and a second end edge opposed thereto, the first and the second longitudinal edges being configured to contact the legs of the wearer, and the first and the second end edges being structured and configured to contact the waist of the wearer; and
  b) at least one elastomeric side panel carried by the containment assembly and extending outwardly from the first longitudinal edge of the containment assembly adjacent the first end edge of the containment assembly, the at least one elastomeric side panel including an inner region having at least one discontinuity for dividing a tensile force applied to the at least one elastomeric side panel into a waist-directing force and a leg-directing force wherein the at least one discontinuity is surrounded by the inner region of the at least one elastomeric side panel, wherein the at least one discontinuity is defined by at least one cut line, wherein the at least one cut line is disposed substantially parallel with a first lateral edge of the at least one elastomeric side panel, wherein the at least one elastomeric side panel farther includes a waist region and a leg region separated by the at least one discontinuity, wherein the waist region is configured to transmit a waist-directing force, and the leg region is configured to transmit a leg-directing force, and wherein the waist region has an extensibility varying from about 5 g/mm to about 50 g/mm and the leg region has an extensibility varying from about 1 g/mm to about 30 g/mm;

wherein the disposable article further comprises a second cut line and a third cut line;

wherein the second cut line extends substantially parallel to a lateral centerline of the at least one elastomeric side panel, and the third cut line extends substantially parallel to a second lateral edge of the at least one elastomeric side panel.

2. The disposable article in accordance with claim 1 wherein the waist region has a greater width than the leg region.

3. The disposable article in accordance with claim 1 wherein the at least one cut line is rectilinear.

4. The disposable article in accordance with claim 1 wherein the at least one cut line is curvilinear.

5. The disposable article in accordance with claim 1 wherein the waist-directing force in the waist region of the at least one elastomeric side panel extends at an angle ranging from about 0 to about 45 relative to a lateral centerline of the disposable article, and wherein the leg-directing force in the leg region of the at least one elastomeric side panel extends at an angle ranging from about 10° to about 35° relative to the latent centerline of the disposable article.

6. The disposable article in accordance with claim 1 wherein the waist-directing force in the waist region of the at least one elastomeric side panel extends at an angle ranging from about 10° to about 15° relative to a lateral centerline of the disposable article, and wherein the leg-directing force in the leg region of the at least one elastomeric side panel extends at an angle ranging from about 20° to about 30° relative to the lateral centerline of the disposable article.

7. The disposable article in accordance with claim 1 wherein the at least one elastomeric side panel has an extensibility ranging from about 1 g/mm to about 50 g/mm.

8. The disposable article in accordance with claim 1 wherein the at least one elastomeric side panel is elastic and has an elasticity of at least about 5%.

* * * * *

UNITED STATES PATENT AND TRADEMARK OFFICE
CERTIFICATE OF CORRECTION

PATENT NO. : 7,217,260 B2  Page 1 of 1
APPLICATION NO. : 09/773241
DATED : May 15, 2007
INVENTOR(S) : John C. Molander et al.

It is certified that error appears in the above-identified patent and that said Letters Patent is hereby corrected as shown below:

<u>Column 15</u>

Line 7, delete "farther" and insert -- further --.

<u>Column 16</u>

Line 4, delete "0" and add -- 0° --.

<u>Column 16</u>

Line 4, delete "45" and insert -- 45° --.

<u>Column 16</u>

Line 8, delete "latent" and insert -- lateral --.

Signed and Sealed this

Twenty Second Day of April, 2008

JON W. DUDAS
*Director of the United States Patent and Trademark Office*